US011323846B2

(12) United States Patent
Sabripour et al.

(10) Patent No.: US 11,323,846 B2
(45) Date of Patent: May 3, 2022

(54) DEVICE, SYSTEM AND METHOD FOR EVACUATION TASK MANAGEMENT

(71) Applicant: MOTOROLA SOLUTIONS, INC., Chicago, IL (US)

(72) Inventors: Shervin Sabripour, Plantation, FL (US); Jared Knapp, Fort Lauderdale, FL (US); John B. Preston, Plantation, FL (US)

(73) Assignee: MOTOROLA SOLUTIONS, INC., Chicago, IL (US)

( * ) Notice: Subject to any disclaimer, the term of this patent is extended or adjusted under 35 U.S.C. 154(b) by 799 days.

(21) Appl. No.: 16/203,900

(22) Filed: Nov. 29, 2018

(65) Prior Publication Data

US 2020/0175639 A1 Jun. 4, 2020

(51) Int. Cl.
*H04W 4/029* (2018.01)
*G06Q 90/00* (2006.01)
(Continued)

(52) U.S. Cl.
CPC .......... *H04W 4/029* (2018.02); *G01C 21/206* (2013.01); *G02B 27/01* (2013.01); *G06Q 90/205* (2013.01);
(Continued)

(58) Field of Classification Search
CPC ......... H04W 4/029; H04W 4/90; H04W 4/30; G01C 21/206; G02B 27/01;
(Continued)

(56) References Cited

U.S. PATENT DOCUMENTS 6,317,042 B1 * 11/2001 Engelhorn ............. G08B 7/062
340/288
7,035,650 B1 * 4/2006 Moskowitz ............ G01C 21/20
340/995.23
(Continued)

FOREIGN PATENT DOCUMENTS

JP 2006201961 A * 8/2006
JP 2008225630 A * 9/2008 ............. G08B 7/066
JP 2013073300 A * 4/2013

OTHER PUBLICATIONS

Chittaro et al. Presenting evacuation instructions on mobile devices by means of location-aware 3D virtual environments. In Proceedings of the 10th international conference on Human computer interaction with mobile devices and services (MobileHCI '08). (Year: 2008).*

(Continued)

*Primary Examiner* — Nathan A Mitchell
(74) *Attorney, Agent, or Firm* — Perry + Currier, Inc.

(57) ABSTRACT

A device, system and method for evacuation task management is provided. A computing device: receives initial sensor data from sensors of a building; generates respective evacuation instructions for evacuating persons and objects from the building for each of responders, the respective evacuation instructions generated from rules for evacuating the building and the initial sensor data, each person or object associated with at least one of the sensors; transmits the respective evacuation instructions to a respective communication device of the responders; monitors updated sensor data from the sensors during evacuation of the building and location information associated with each of the responders, to track compliance with the respective evacuation instructions; and transmits updated respective evacuation instructions to the respective communication device of one or more of the responders, the updated respective evacuation instruc- (Continued)

tions based on monitored updated sensor data and monitored location information received after transmitting the respective evacuation instructions.

20 Claims, 5 Drawing Sheets

(51) Int. Cl.
  *G01C 21/20* (2006.01)
  *H04W 4/90* (2018.01)
  *G16H 10/60* (2018.01)
  *G16H 20/10* (2018.01)
  *G02B 27/01* (2006.01)

(52) U.S. Cl.
  CPC ............ *G16H 10/60* (2018.01); *G16H 20/10* (2018.01); *H04W 4/90* (2018.02); *G02B 2027/014* (2013.01)

(58) Field of Classification Search
  CPC ............ G02B 2027/014; G02B 27/017; G02B 2027/0138; G06Q 90/205; G16H 10/60; G16H 20/10; G16H 40/20; G16H 40/67
  See application file for complete search history.

(56) References Cited

U.S. PATENT DOCUMENTS

| | | | | |
|---|---|---|---|---|
| 7,579,945 | B1* | 8/2009 | Richter | G08B 25/14 |
| | | | | 340/286.14 |
| 8,332,063 | B2 | 12/2012 | Moshier | |
| 9,080,883 | B2* | 7/2015 | Frey | G08B 7/066 |
| 9,898,912 | B1* | 2/2018 | Jordan, II | G08B 17/10 |
| 10,026,278 | B1* | 7/2018 | Asaro | G08B 7/062 |
| 10,026,279 | B1* | 7/2018 | Beller | G08B 7/066 |
| 10,529,199 | B2* | 1/2020 | Wedig | G08B 17/10 |
| 10,692,339 | B2* | 6/2020 | Beller | G09B 21/006 |
| 10,769,741 | B2* | 9/2020 | Braun | G16H 40/20 |
| 10,769,902 | B1* | 9/2020 | Kronz | G08B 7/066 |
| 2004/0172277 | A1* | 9/2004 | Dione | G06Q 30/02 |
| | | | | 705/324 |
| 2008/0122609 | A1* | 5/2008 | Mannisto | G08B 25/016 |
| | | | | 340/500 |
| 2009/0138353 | A1* | 5/2009 | Mendelson | G01S 5/02 |
| | | | | 705/14.39 |
| 2009/0170468 | A1* | 7/2009 | Kane | G01G 21/20 |
| | | | | 455/404.2 |
| 2009/0201161 | A1 | 8/2009 | Stevens et al. | |
| 2009/0270065 | A1* | 10/2009 | Hamada | G01S 5/12 |
| | | | | 455/404.1 |
| 2011/0195687 | A1* | 8/2011 | Das | H04W 4/02 |
| | | | | 455/404.2 |
| 2013/0116922 | A1* | 5/2013 | Cai | G01C 21/206 |
| | | | | 701/515 |
| 2013/0147604 | A1* | 6/2013 | Jones, Jr | G08B 7/066 |
| | | | | 340/6.1 |
| 2014/0167969 | A1* | 6/2014 | Wedig | G08B 7/066 |
| | | | | 340/584 |
| 2014/0222329 | A1* | 8/2014 | Frey | G01C 21/206 |
| | | | | 701/423 |
| 2014/0293865 | A1* | 10/2014 | Shi | G08B 21/10 |
| | | | | 370/312 |
| 2015/0179038 | A1 | 6/2015 | Daniel et al. | |
| 2016/0140526 | A1 | 5/2016 | Cummins et al. | |
| 2017/0024839 | A1* | 1/2017 | Klein | H04W 4/029 |
| 2017/0032632 | A1* | 2/2017 | Joseph | H04W 4/02 |
| 2018/0096573 | A1 | 4/2018 | Tadano | |
| 2018/0216940 | A1* | 8/2018 | Pattar | H04B 17/318 |
| 2020/0364819 | A1* | 11/2020 | de Hoog | G06F 16/29 |

OTHER PUBLICATIONS

Atila, Umit, Yasin Ortakci, Kasim Ozacar, Emrullah Demiral, and Ismail R. Karas. "SmartEscape: A Mobile Smart Individual Fire Evacuation System Based on 3D Spatial Model" ISPRS International Journal of Geo-Information 7, No. 6: 223. 2018. (Year: 2018).*

Wu et al. A Framework of Intelligent Evacuation Guidance System for Large Building. 5th International Conference on Civil, Architectural and Hydraulic Engineering (ICCAHE 2016). pp. 695-701. 2016. (Year: 2016).*

D. Pojee et al. "Intelligent disaster warning and response system with dynamic route selection for evacuation," 2017 International Conference on Intelligent Sustainable Systems (ICISS), 2017, pp. 1-5. (Year: 2017).*

Poy et al. "A Cloud-Enabled Building and Fire Emergency Evacuation Application," in IEEE Cloud Computing, vol. 1, No. 4, pp. 40-49, Nov. 2014. (Year: 2014).*

Liu et al. "Intelligent indoor emergency evacuation systems: Reference architecture and data requirements," 2016 Future Technologies Conference (FTC), 2016, pp. 600-609. (Year: 2016).*

* cited by examiner

DEVICE, SYSTEM AND METHOD FOR EVACUATION TASK MANAGEMENT

BACKGROUND OF THE INVENTION

During emergency evacuation procedures of buildings, such as hospitals, nursing homes, in-home care centers, and the like, there are multiple "rules" that are in place as part of the procedures, which are to be followed by responders (e.g. fire fighters) responding to the emergency evacuation. However, when there are multiple assets (e.g. persons and/or objects) to be evacuated, it can be challenging to coordinate such an emergency evacuation with the responders. Further, existing evacuation assistance systems store entire sets of building floor plans and asset lists which must be transmitted from the database in which they are stored to the edge devices of evacuation personnel, consuming substantial processing power and bandwidth at the database, and furthermore must be received at the edge devices consuming substantial bandwidth and processing power there as well, in addition to power and processing power consumed in displaying and parsing through the data at each receiving device to locate the particular information needed at each individual edge device.

BRIEF DESCRIPTION OF THE SEVERAL VIEWS OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION OF THE INVENTION

In light of the above-noted technical problems in existing evacuation assistance systems, what is needed is an improved technical system in which only initial building/location data and asset (person and/or object) data that is particularly needed by a particular edge device associated with an evacuation personnel is transmitted from an evacuation assistance database to each edge device, and which monitors compliance with initial instructions to determine if additional and/or modified building data and asset data needs to be provided to any particular one of the edge devices that has already received the initial data, thereby reducing bandwidth consumption, processing power requirements, and input interface interactions necessary to direct a user to or across a particular evacuation path to evacuate assets from a building or location.

An aspect of the specification provides a computing device comprising: a communication unit configured to communicate with: sensors distributed throughout a building; and communication devices associated with responders; and a controller communicatively coupled to the communication unit and to a memory storing rules for evacuating the building, the controller configured to: receive, via the communication unit, initial sensor data from the sensors; generate respective evacuation instructions for evacuating one or more of persons and objects from the building for each of the responders, the respective evacuation instructions generated from the rules for evacuating the building and the initial sensor data, each person or object associated with at least one of the sensors; transmit, via the communication unit, the respective evacuation instructions to a respective communication device of each of the responders; monitor, via the communication unit, updated sensor data from the sensors during evacuation of the building and location information associated with each of the responders, to track compliance with the respective evacuation instructions by the responders; and transmit, via the communication unit, updated respective evacuation instructions to the respective communication device of one or more of the responders, the updated respective evacuation instructions based on monitored updated sensor data and monitored location information received after transmitting the respective evacuation instructions.

Another aspect of the specification provides a method comprising: receiving, at a computing device, initial sensor data from sensors distributed throughout a building; generating, at the computing device, respective evacuation instructions for evacuating one or more of persons and objects from the building for each of responders, the respective evacuation instructions generated from rules for evacuating the building and the initial sensor data, each person or object associated with at least one of the sensors; transmitting, at the computing device, the respective evacuation instructions to a respective communication device of each of the responders; monitoring, at the computing device, updated sensor data from the sensors during evacuation of the building and location information associated with each of the responders, to track compliance with the respective evacuation instructions by the responders; and transmitting, at the computing device, updated respective evacuation instructions to the respective communication device of one or more of the responders, the updated respective evacuation instructions based on monitored updated sensor data and monitored location information received after transmitting the respective evacuation instructions.

Figure 1:
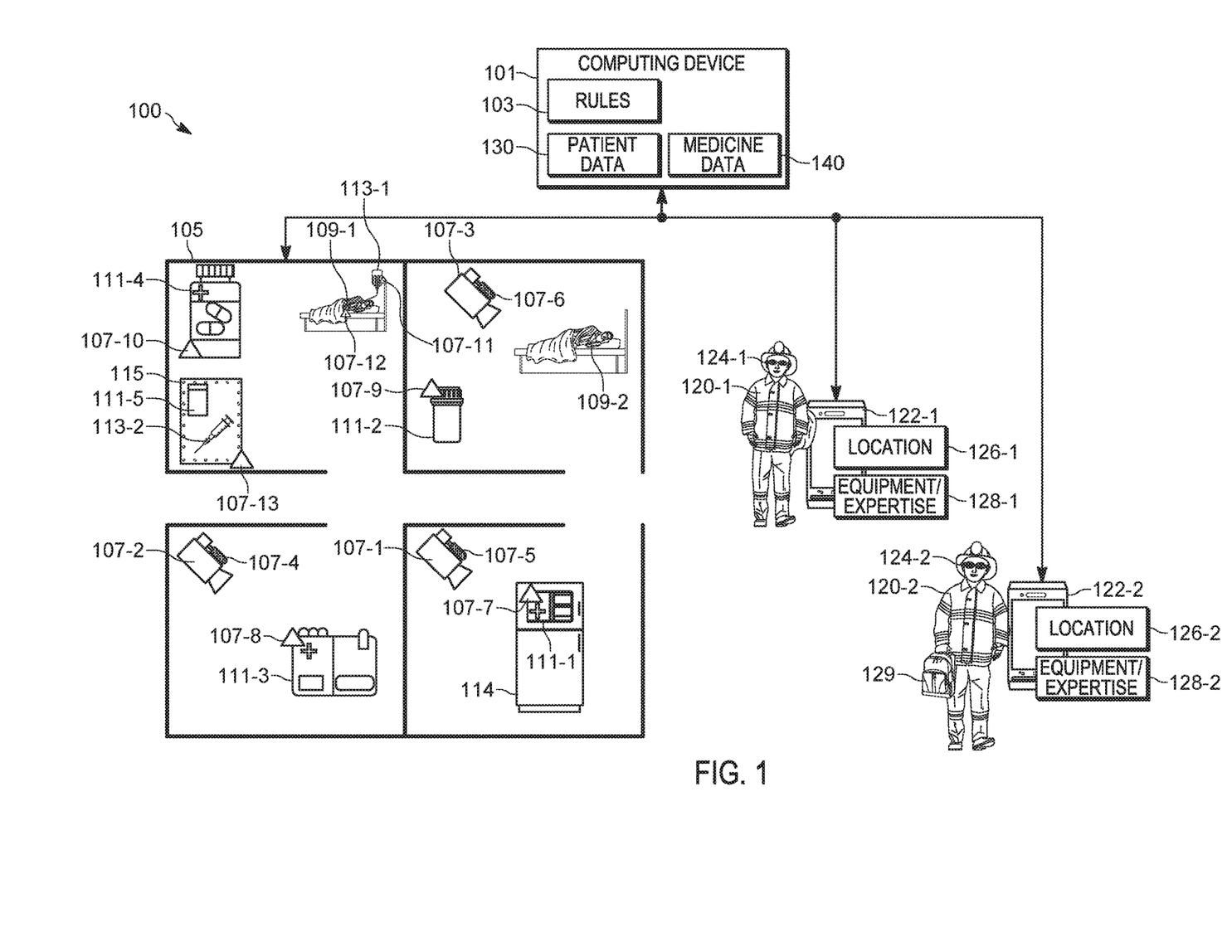
FIG. 1 is a system for evacuation task management, in accordance with some examples.

Attention is directed to FIG. 1, which depicts an example system 100 for evacuation task management. The system 100 comprises a computing device 101 that has access to rules 103 for evacuating a building 105, which is schematically depicted as a plurality of rooms, but may include more or less than the depicted number of rooms, and more than one floor.

The computing device 101 is further in communication with sensors 107-1, 107-2, 107-3, 107-4, 107-5, 107-6, 107-7, 107-8, 107-9, 107-10, 107-11, 107-12, 107-13 distributed throughout the building 105. The sensors 107-1, 107-2, 107-3, 107-4, 107-5, 107-6, 107-7, 107-8, 107-9, 107-10, 107-11, 107-12, 107-13 are interchangeably referred to hereafter, collectively, as the sensors 107 and, generically, as a sensor 107.

In the depicted example, the building 105 comprises a hospital with patients 109-1, 109-2 in respective hospital rooms, and medicines 111-1, 111-2, 111-3, 111-4, 111-5 stored throughout. The patient 109-1 is associated with particular medicines 111-4, 111-5, and medical devices 113-1, 113-2, and the patient 109-2 is associated with particular medicine 111-2. For example, the medicines 111-4, 111-5 may have been prescribed to the patient 109-1, and the medicine 111-2 may have been prescribed to the patient 109-2. The medical device 113-1, as depicted, comprises an intravenous (IV) drip for the patient 109-1, and the medical device 113-2 comprises a needle, which may be used to administer the medicine 111-5. As depicted, the medicine 111-2 and the medical device 113-2 are stored in a drawer 115. As depicted, the medicine 111-1 is being stored in a refrigerator 114, and the like; for example, the medicine 111-1 may be required to be refrigerated to maintain its effectiveness.

The patients 109-1, 109-2 are interchangeably referred to hereafter, collectively, as the patients 109 and, generically, as a patient 109. The medicines 111-1, 111-2, 111-3, 111-4, 111-5 are interchangeably referred to hereafter, collectively, as the medicines 111 and, generically, as medicine 111. The medical devices 113-1, 113-2 are interchangeably referred to hereafter, collectively, as the medical devices 113 and, generically, as a medical device 113.

As depicted, the sensors 107-1, 107-2, 107-3 each comprise a respective camera and/or video camera. Each camera generates sensor data in the form of images.

As depicted, the sensors 107-4, 107-5, 107-6, 107-7 each comprise a respective microphone. Each microphone generates sensor data in the form of audio.

As depicted, the sensors 107-8, 107-9, 107-10, 107-11 each comprise a respective asset tracking sensor and/or an internet-of-things sensor attached to respective medicine 111 and/or a respective medical device 113, and which tracks the location and/or state (e.g. binary data such as opened, closed, and the like or more complex state information such as a measured amount of medication (in mL or capsules) remaining for distribution and the like) of the respective medicine 111 and/or medical device 113. Hence, each respective asset tracking sensor and/or internet-of-things sensor generates sensor data in the form of asset tracking data and/or internet-of-things sensor data which may include, but is not limited to, locations and/or state of respective medicine and/or medical device 113. Herein, however, both persons and objects may interchangeably be referred to as assets, for example to be evacuated in an emergency evacuation. Furthermore, a person in the building 105 may also be associated (e.g. wearing) a respective asset tracking sensor and/or an internet-of-things sensor.

As depicted, the sensor 107-12 comprises a biometric sensor worn by the patient 109-1. The biometric sensor generates sensor data in the form of biometric sensor data which may include temperature, heartrate, and the like of the patient 109-1; in some examples the biometric sensor worn by the patient 109-1 may also generate sensor data in the form of a location of the patient 109-1. Hence, the sensor 107-12 may also comprise an asset tracking sensor and/or an internet-of-things sensor.

As depicted, the sensor 107-13 comprises a binary sensor which generates binary data indicative of one or more of drawers, doors and windows being open or closed. For example, as depicted, the sensor 107-13 comprises a drawer sensor attached to the drawer 115, and which indicates whether the drawer 115 is open or closed. As depicted, neither of the medicine 111-5 nor the medical device 113-2, in the drawer 115, have sensors 107 attached thereto. Hence, binary data from the sensor 107-13 may be used to determine that the drawer 115 has been opened and hence that the medicine 111-5 and the medical device 113-2 therein have been retrieved. However, the system 100 may comprises one or more drawer sensors, door sensors and window sensors generating respective binary data indicative of one or more of drawers, doors and windows being open or closed.

Indeed, the system 100 may include any suitable number of sensors 107 which may be used to track assets and/or locations of assets and/or which may be used to track locations of persons and/or objects (e.g. medicines 111, medical devices 113, and/or any other suitable objects) in the building 105.

In general, in FIG. 1, an incident (e.g. a fire) may be occurring in the building 105 that has resulted in responders 120-1, 120-2 (e.g. fire fighters) being dispatched to the building 105 to evacuate the patients 109, the medicines 111, and the medical devices 113 and/or any other suitable assets in the building 105. For example, the responders 120-1, 120-2 may also evacuate other people in the building 105, such as nurses, workers, doctors, visitors and the like.

As depicted, each of the responders 120-1, 120-2 are carrying a respective communication device 122-1, 122-2, and wearing respective heads-up display (HUD) communication devices 124-1, 124-2. Furthermore, each of the communication devices 122-1, 122-2 may be determining a respective location 126-1, 126-2 thereof (e.g. via a respective location determining device such as Global Positioning (GPS) system and the like or an indoor positioning system (IPS) such as using wireless anchor points with known indoor locations and relative signal strength measurements taken at edge devices to determine relative indoor positions, among other commercial indoor locationing techniques that may rely upon magnetic variations caused by a buildings steel structure or that may rely upon inertial detection and dead reckoning, for example). Each of the communication devices 122-1, 122-2 may further store (e.g. in a respective memory) respective data 128-1, 128-2 indicating equipment and/or expertise of a respective responder 120-1, 120-2. For example, the responder 120-1 may be trained in cardiopulmonary resuscitation (CPR) which may be indicated in the data 128-1. Similarly, the responder 120-2 may be carrying an insulated bag 129 (e.g. suitable for carrying the medicine 111-1 needing refrigeration), and which may be indicated in the data 128-2.

The responders 120-1, 120-2 are interchangeably referred to hereafter, collectively, as the responders 120 and, generically, as a responder 120. The communication devices 122-1, 122-2 are interchangeably referred to hereafter, collectively, as the communication devices 122 and, generically, as a communication device 122. The HUD communication devices 124-1, 124-2 are interchangeably referred to hereafter, collectively, as the HUD communication devices 124 and, generically, as HUD communication device 124. The data 128-1, 128-2 is interchangeably referred to hereafter, collectively, as the data 128 and, generically, as a set of data 128 and/or the data 128.

The responders 120 may be any suitable responders such as fire fighters, emergency medical technicians, police officers, security guards, nurses, doctors, and the like who may have been assigned and/or dispatched to evacuate the building 105. Furthermore, one or more of the HUD communication device 124 may be optional. Furthermore, in some examples, the HUD communication device 124 may form a personal area network (PAN) with a respective communication device 122. In yet further examples, a communication device 122 may be replaced with a HUD communication device 124 and/or a communication device 122 may comprise a HUD communication device 124.

In general, the computing device 101 is configured to communicate with: the sensors 107 distributed throughout the building 105; and the communication devices 122 associated with responders 120. For example, as depicted, the computing device 101 is in communication with the sensors 107 and the communication devices 122 via communication links depicted, in FIG. 1, as double headed arrows. To reduce complexity in FIG. 1, communication links to the sensors 107 are generally depicted as one double-headed arrow between the computing device 101 and the building 105; the communication links may be wired or wireless as desired, and may be via any suitable communication network (not depicted). In some embodiments, the computing device 101 may communicate directly with sensors 107 having an assigned network or hardware address such that a bi-directional wired and/or wireless communication link can be established, or may communicate indirectly with sensors 107 in an embodiment, for example, in which a radio frequency identification (RFID) reader positioned in a room has an assigned network or hardware address such that a bi-directional wired and/or wireless communication link can be established between the computing device 101 and the RFID reader, and the RFID reader then interfaces with one or more RFID sensors positioned in the room and on behalf of the computing device 101. Other examples are possible as well.

While not depicted, the computing device 101 may be in communication with other types of sensors in the building 105; for example, the building 105 may include smoke and/or heat sensors, and the like, which may communicate smoke and/or heat sensor data to the computing device 101 such that a route of, for example, a fire through the building 105 may be tracked.

The rules 103 for evacuating the building 105 may comprise one or more of electronically stored: one or more evacuation routes; a priority of human assets (e.g. the patients 109) to be evacuated from the building 105; and a priority of physical assets (e.g. objects and/or the medicines 111 and/or the medical devices 113) to be evacuated from the building 105. Hence, the rules 103 generally define an evacuation plan of the building 105 including, but not limited to, a map of the building 105, generic evacuation routes for the building 105 (e.g. locations of emergency exits and routes thereto from various rooms in the building 105), and the like. The rules 103 may further define rules for conducting the evacuation by the responders 120; for example, the rules 103 may define that refrigerated medicines 111 are to be prioritized over non-refrigerated medicines 111, and that patients 109 are to be evacuated with associated medicines 111 and medical devices 113. However, in other embodiments, the rules 103 may not make reference to specific patients 109 and/or medicines 111 and/or medical devices 113.

As depicted, the computing device 101 may electronically store patient data 130 and/or medicine data 140. The patient data 130 may include patient records including, but not limited to, specific medicines 111 and/or medical devices 113 associated with each patient 109, respective locations (e.g. room numbers in the building 105, tracked or reported GPS or IPS locations, and the like) of the patients 109, sensors 107 associated with the patients 109, and the like. Similarly, the medicine data 140 may include respective locations of the medicines 111 (e.g. room numbers in the building 105, tracked or reported GPS or IPS locations, and the like), information for storing the medicines 111 (e.g. whether a medicine is to be refrigerated or not, and the like).

While not depicted, the rules 103, data 128, the patient data 130, and/or the medicine data 140 may alternatively be electronically stored at a memory of the computing device 101 and/or at an external memory to which the computing device 101 has access; such an external memory may include, but is not limited to, one or more databases storing patient records, medicine records, responder personnel records, and the like.

While the present specification is described with respect to the building 105 being a hospital, and the like, and assets to be evacuated being the patients 109, the medicines 111, and the medical devices 113, in other examples, the building 105 may comprise any suitable type of building (e.g. an office or an apartment building), and the assets to be evacuated may comprise workers and/or residents in the building, and/or any suitable objects in the building, such as important objects and/or documents, and the like. The rules 103 may hence be adapted for such scenarios and, similarly, the patient data 130 and the medicine data 140 may be replaced with data that indicates locations of people in the building (e.g. disabled people in particular apartments and/or office, and the like), locations of important objects and/or documents (e.g., explosive or hazardous chemical containers or executed legal documents), and the like.

Figure 2:
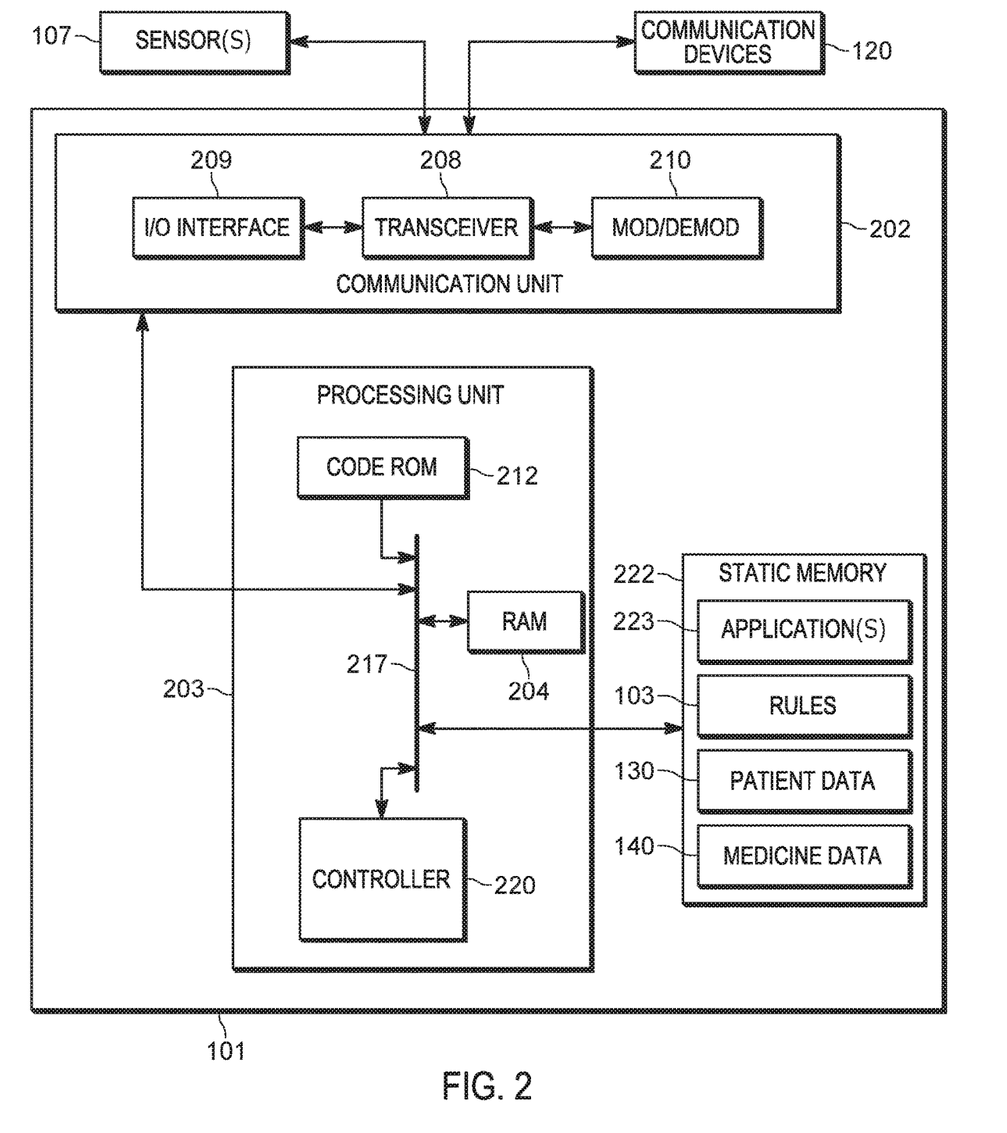
FIG. 2 is a device diagram showing a device structure of a computing device for evacuation task management, in accordance with some examples.

Attention is next directed to FIG. 2, which depicts a schematic block diagram of an example of the computing device 101.

In general, the computing device 101 may comprise a server and/or cloud-based computing device comprising: a communications unit 202, a processing unit 203, a Random-Access Memory (RAM) 204, one or more wireless transceivers 208, one or more wired and/or wireless input/output (I/O) interfaces 209, a combined modulator/demodulator 210, a code Read Only Memory (ROM) 212, a common data and address bus 217, a controller 220, and a static memory 222 storing at least one application 223, and optionally the rules 103, the patient data 130 and the medicine data 140. However, the rules 103, the patient data 130 and the medicine data 140 may be stored at another memory to which the computing device 101 has access (e.g. via the communications unit 202).

Hereafter, the at least one application 223 will be interchangeably referred to as the application 223. Furthermore, each of the memories 212, 222 comprise non-transitory memories and/or non-transitory computer readable mediums.

While not depicted, the computing device 101 may further comprise any other suitable components including, but not limited to, one or more of input devices display screens, speakers, microphones and the like.

As shown in FIG. 2, the computing device 101 includes the communications unit 202 coupled to the common data and address bus 217 of the processing unit 203.

The processing unit 203 may include the code Read Only Memory (ROM) 212 coupled to the common data and address bus 217 for storing data for initializing system components. The processing unit 203 may further include the controller 220 coupled, by the common data and address bus 217, to the Random-Access Memory 204 and the static memory 222.

The communications unit 202 may include one or more wired and/or wireless input/output (I/O) interfaces 209 that are configurable to communicate with the sensors 107 and the communication devices 122 via any suitable wired or wireless communication links. For example, the communication unit 202 may include one or more transceivers 208 and/or wireless transceivers for communicating with the sensors 107 and the communication devices 122. The one or more transceivers 208 may include, but are not limited to, one or more of a digital mobile radio (DMR) transceiver, a Project 25 (P25) transceiver, a terrestrial trunked radio (TETRA) transceiver, a Bluetooth transceiver, a Wi-Fi transceiver, for example operating in accordance with an IEEE 802.11 standard (e.g., 802.11a, 802.11b, 802.11g), an LTE (Long-Term Evolution) transceiver and/or other types of GSM (Global System for Mobile communications) transceivers, a Worldwide Interoperability for Microwave Access (WiMAX) transceiver, for example operating in accordance with an IEEE 802.16 standard, and/or another similar type of wireless transceiver.

The communications unit 202 may optionally include one or more wireline transceivers 208, such as an Ethernet transceiver, a USB (Universal Serial Bus) transceiver, or similar transceiver configurable to communicate via a twisted pair wire, a coaxial cable, a fiber-optic link, or a similar physical connection to a wireline network. The transceiver 208 is also coupled to a combined modulator/demodulator 210.

The controller 220 may include ports (e.g. hardware ports) for coupling to other hardware components.

The controller 220 includes one or more logic circuits, one or more processors, one or more microprocessors, one or more ASIC (application-specific integrated circuits) and one or more FPGA (field-programmable gate arrays), and/or another electronic device. In some examples, the controller 220 and/or the computing device 101 is not a generic controller and/or a generic device, but a device specifically configured to implement functionality for evacuation task management. For example, in some examples, the computing device 101 and/or the controller 220 specifically comprises a computer executable engine configured to implement functionality for evacuation task management.

The static memory 222 is a non-transitory machine readable medium that stores machine readable instructions to implement one or more programs or applications. Example machine readable media include a non-volatile storage unit (e.g. Erasable Electronic Programmable Read Only Memory ("EEPROM"), Flash Memory) and/or a volatile storage unit (e.g. random-access memory ("RAM")). In the example of FIG. 2, programming instructions (e.g., machine readable instructions) that implement the functional teachings of the computing device 101 as described herein are maintained, persistently, at the memory 222 and used by the controller 220, which makes appropriate utilization of volatile storage during the execution of such programming instructions.

Figure 3:
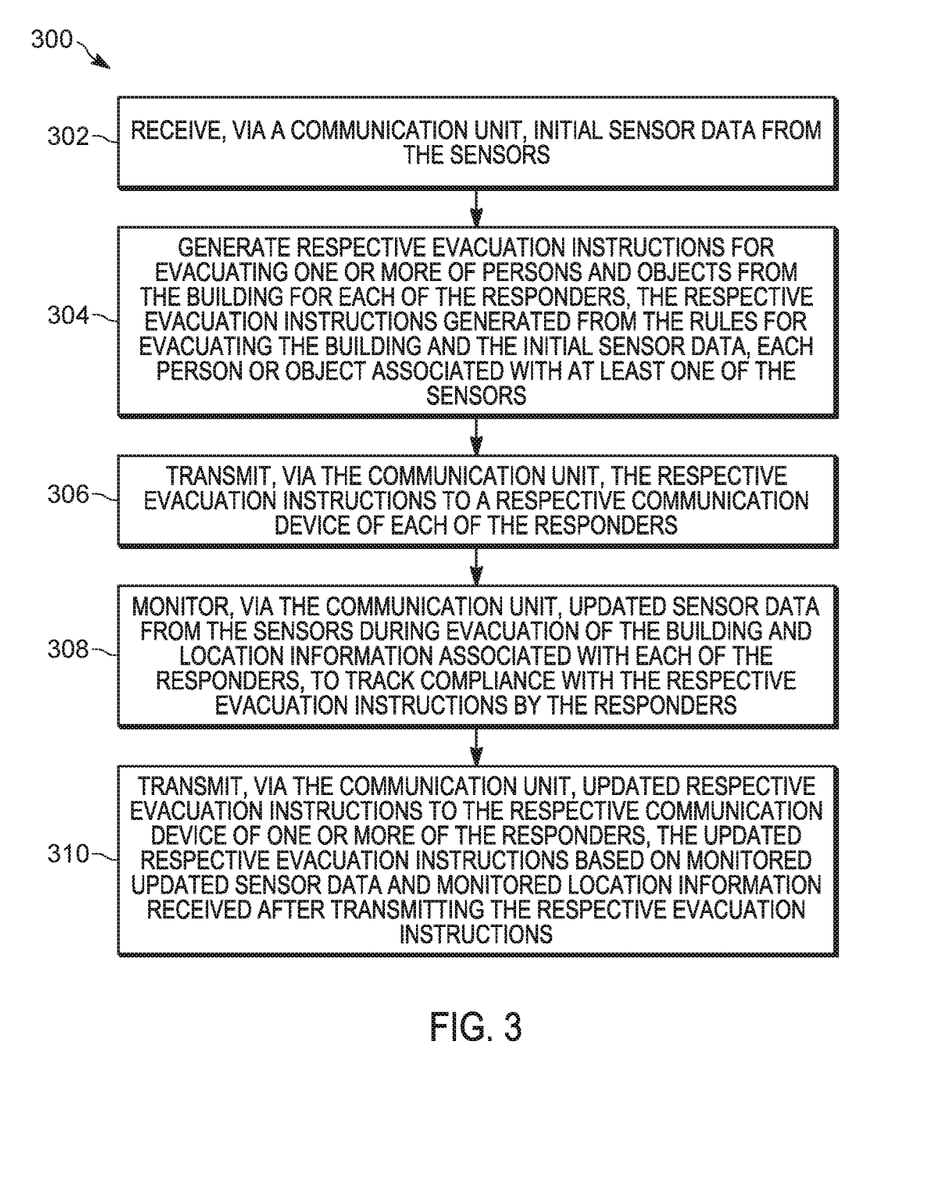
FIG. 3 is a flowchart of a method for evacuation task management, in accordance with some examples.

In particular, the memory 222 stores instructions corresponding to the at least one application 223 that, when executed by the controller 220, enables the controller 220 to implement functionality for evacuation task management including, but not limited to, some or all of the blocks of the method set forth in FIG. 3.

In an embodiment, when the controller 220 executes the one or more applications 223, the controller 220 is enabled to: receive, via the communication unit 202, initial sensor data from the sensors 107; generate respective evacuation instructions for evacuating one or more of persons and objects from the building 105 for each of the responders 120, the respective evacuation instructions generated from the rules 103 for evacuating the building 105 and the initial sensor data, each person or object associated with at least one of the sensors 107; transmit, via the communication unit 202, the respective evacuation instructions to a respective communication device 122 of each of the responders 120; monitor, via the communication unit 202, updated sensor data from the sensors 107 during evacuation of the building 105 and location information associated with each of the responders 120, to track compliance with the respective evacuation instructions by the responders 120; and transmit, via the communication unit 202, updated respective evacuation instructions to the respective communication device 122 of one or more of the responders 120, the updated respective evacuation instructions based on monitored updated sensor data and monitored location information received after transmitting the respective evacuation instructions.

The application 223 may include machine learning and/or deep-learning based algorithms and/or neural networks, and the like, which have been trained and/or configured to: generate respective evacuation instructions for evacuating one or more of persons and objects from the building 105 for each of the responders 120, the respective evacuation instructions generated from the rules 103 for evacuating the building 105 and the initial sensor data; and/or; track compliance with the respective evacuation instructions by the responders 120 based on updated sensor data from the sensors 107 during evacuation of the building 105 and location information associated with each of the responders 120; and/or generate updated respective evacuation instructions based on monitored updated sensor data and monitored location information received after transmitting the respective evacuation instructions.

The one or more machine learning algorithms and/or deep learning algorithms and/or neural networks of the application 223 may include, but are not limited to: a generalized linear regression algorithm; a random forest algorithm; a support vector machine algorithm; a gradient boosting regression algorithm; a decision tree algorithm; a generalized additive model; neural network algorithms; deep learning algorithms; evolutionary programming algorithms; Bayesian inference algorithms, reinforcement learning algorithms, and the like. However, any suitable combination of one or more machine learning algorithms and/or deep learning algorithms and/or neural networks is within the scope of the present specification.

However, generalized linear regression algorithms, random forest algorithms, support vector machine algorithms, gradient boosting regression algorithms, decision tree algorithms, generalized additive models, and the like may be preferred over neural network algorithms, deep learning algorithms, evolutionary programming algorithms, and the like, in some public safety environments. However, any suitable machine learning algorithm and/or deep learning algorithm is within the scope of present examples.

Furthermore, the application 223 may include, but are not limited to, algorithms for one or more of: video analytics algorithms, object-matching analytics algorithms, action-matching analytics algorithms, two-dimensional image matching, three-dimensional model matching, and the like, for example to determine from images from the sensors 107 whether persons and/or objects are being evacuated and/or locations of persons and/or objects (including, but not limited to, the patients 109 and/or the responders 120).

While details of the sensors 107 and the communication devices 122 are not depicted, each of the sensors 107 and the communication devices 122 may have components similar to the computing device 101 adapted, however, for the functionality of the sensors 107 and the communication devices 122. Each of the sensors 107 is further adapted with components for their respective sensor functionality.

Attention is now directed to FIG. 3, which depicts a flowchart representative of a method 300 for evacuation task management. The operations of the method 300 of FIG. 3 correspond to machine readable instructions that are executed by the computing device 101, and specifically the controller 220 of the computing device 101. In the depicted example, the instructions represented by the blocks of FIG. 3 are stored at the memory 222 for example, as the application 223. The method 300 of FIG. 3 is one way in which the controller 220 and/or the computing device 101 and/or the system 100 may be configured. Furthermore, the following discussion of the method 300 of FIG. 3 will lead to a further understanding of the system 100, and its various components. However, it is to be understood that the method 300 and/or the system 100 may be varied, and need not work exactly as discussed herein in conjunction with each other, and that such variations are within the scope of present examples.

The method 300 of FIG. 3 need not be performed in the exact sequence as shown and likewise various blocks may be performed in parallel rather than in sequence. Accordingly, the elements of method 300 are referred to herein as "blocks" rather than "steps." The method 300 of FIG. 3 may be implemented on variations of the system 100 of FIG. 1, as well.

At a block 302, the controller 220 receives, via the communication unit 202, initial sensor data from the sensors 107. For example, the sensors 107 may be configured to periodically transmit sensor data and/or the controller 220 may be configured to periodically request the sensor data from the sensors 107.

At a block 304, the controller 220 generates respective evacuation instructions for evacuating one or more of persons and objects from the building 105 for each of the responders 120, the respective evacuation instructions generated from the rules 103 for evacuating the building 105 and the initial sensor data, each person or object associated with at least one of the sensors 107. The persons and object may respectively comprise the patients 109, and the medicines 111 and/or medical devices 113.

The respective evacuation instructions may comprise instructions for evacuating the building 105 for each of the responders, and which may include a respective route through the building 105 that each of the responders 120 is to follow (e.g. based on a map of the building 105 in the rules 103), and/or instructions for following a respective route through the building 105. The respective evacuation instructions may further include a list of persons and associated objects that a respective responder 120 is to evacuate (and/or locations of the persons and associated objects and/or instructions for retrieving the persons and objects). The respective evacuation instructions may further include an order of the persons and objects that a respective responder 120 is to evacuate (e.g. as based on the rules 103, and the patient data 130 and/or the medicine data 140).

The respective evacuation instructions may further be generated from one or more of equipment and expertise of a respective responder accessed (e.g. as the data 128) at one or more of the memory 222 (and/or an external memory) and the respective communication device 122 of the respective responder 120. As such, the controller 220 may request the data 128 from the communication devices 122. Indeed, in some examples, when the responders 120 arrive at the building 105, the communication devices 122 may register with the computing device 101 and/or the communication devices 122 may register with the computing device 101 prior to the responders 120 arriving at the building; either way, the computing device 101 may access and/or receive the data 128.

Hence, the evacuation instructions for the responder 120-1 with CPR training may include, but are not limited to, an evacuation route that includes retrieving the patients 109, and an order for picking up the patients 109 and associated medicines 111 and/or medical devices 113. For example, the patient 109-1 may be retrieved prior to the patient 109-2, as the patient 109-1 may be more mobile than the patient 109-2 (e.g. who is attached to the medical device 113-1). Indeed, the rules 103 may indicate that more mobile patients are to be retrieved prior to less mobile patients, and the mobility of the patients 109 may be determined from the patient data 130.

Similarly, the evacuation instructions for the responder 120-2 with the insulated bag 129 may include, but are not limited to, an evacuation route that includes retrieving the medicine 111-1 from the refrigerator 114 and placing the medicine 111-1 into the insulated bag 129. Indeed, the evacuation instructions for the responder 120-2 may include an order in which to evacuate medicines 111. For example, the medicine 111-1 may be retrieved first in the event that power to the building 109 has been lost and the medicine 111-1 may hence be at risk of warming up in the refrigerator 114 after it has lost power.

Indeed, the rules 103 may indicate that refrigerated medicines (and perhaps their associated patients) is to be retrieved prior to non-refrigerated medicines (and perhaps their associated patients), and medicines 111 that are refrigerated may be determined from the medicine data 140.

Hence, the respective evacuation instructions for evacuating the building 105 for each of the responders 120 may comprise one or more of: a route through the building 105; assigned tasks (to place the medicine 111-1 in the insulated bag 129); a list of human assets to evacuate from the building 105 along the route; an order in which to evacuate the human assets on the list of human assets; a list of physical assets to evacuate from the building along the route; and an order in which to evacuate the physical assets on the list of physical assets. Hence, the respective evacuation instructions for evacuating the building 105 for each of the responders 120 may comprise a rules-based prioritization of what assets (e.g. human assets and/or physical assets associated or unassociated with one another) to evacuate first. For example, the order in which to evacuate the human assets on the list of human assets and/or the order in which to evacuate the physical assets on the list of physical assets may represent a priority of the human assets and/or the physical assets, or some combination thereof based on their shared same or similar (next door, within threshold distance of 5-100 ft, etc.) locations.

Furthermore, when generating the respective evacuation instructions, the computing device 101 has access to at least an initial location of each of the responders 120 (e.g. the locations 126). For example, the computing device 101 may access and/or determine the respective locations 126 of the responders 120, by one or more of receiving the locations 126 from the communication devices 122, receiving sensor data in the form of images (e.g. from the sensors 107-1, 107-2, 107-3 (i.e. the cameras)), and the like. In examples where the computing device 101 determines locations from images, the computing device 101 may further have access to locations of the sensors 107-1, 107-2, 107-3 (e.g. as stored in the rules 103; indeed, the sensors 107-1, 107-2, 107-3 may be fixed).

At a block 306, the controller 220 transmits, via the communication unit 202, the respective evacuation instructions to a respective communication device 122 of each of the responders 120. The respective evacuation instructions may be in a format that can be provided visually (e.g. at a display screen) and/or aurally (e.g. via a microphone) at the respective communication device 122. Alternatively, the respective evacuation instructions may be transmitted to a respective HUD communication device 124 (e.g. via the respective communication device 122 when in a PAN, and/or directly); in these examples, the respective evacuation instructions are in a HUD format for the respective HUD communication device 124.

When the communication devices 122 (and/or the HUD communication devices 124) receive the evacuation instructions, the respective responders 120 may then follow the respective evacuation instructions.

At a block 308, the controller 220 monitors, via the communication unit 202, updated sensor data from the sensors 107 during evacuation of the building 105 and location information associated with each of the responders 120, to track compliance with the respective evacuation instructions by the responders 120.

For example, sensor data continues to be received and monitored by the controller 220, and the controller 220 determines from the monitored updated sensor data and the locations of the responders 120 whether the responders 120 are complying with and/or following the respective evacuation instructions. Furthermore, the controller 220 tracks respective locations 126 of the responders 120 as they move through the building 105, for example by continuing to receive respective locations 126 from the communication devices 122, and/or via updated sensor data.

Indeed, as described previously, one or more of the initial sensor data (e.g. received at the block 302 of the method 300) and the monitored updated sensor data (e.g. received at the block 308 of the method 300) comprises one or more of: images from one or more cameras; audio from one or more microphones; asset tracking data from one or more asset tracking sensors; biometric sensor data from one or more biometric sensors; and internet-of-things sensor data from internet-of-things sensors (which may include binary data indicative of one or more of drawers, doors and windows being open or closed, the binary data from one or more drawer sensors, door sensors and window sensors; and which may include more complex state information such as an amount of medication remaining measured in mL or capsules, or other measured state information).

For example, the controller 220 may be further configured to monitor the updated sensor data during evacuation of the building 105 to track compliance with the respective evacuation instructions by the responders 120 by determining one or more of: whether a respective responder 120 is following a respective route through the building provided in the respective evacuation instructions; whether the respective responder 120 is retrieving respective human assets provided in the respective evacuation instructions; and whether the respective responder 120 is retrieving respective physical assets (associated with or unassociated with a particular human asset) provided in the respective evacuation instructions.

At a block 310, the controller 220 transmits, via the communication unit 202, updated respective evacuation instructions to the respective communication device 122 of one or more of the responders 120, the updated respective evacuation instructions based on monitored updated sensor data and monitored location information received after transmitting the respective evacuation instructions.

In particular, the controller 220 may be further configured to: when compliance with the respective evacuation instructions is not occurring for a respective responder 120, include, in the updated respective evacuation instructions for the respective communication device 122 of the respective responder 120, an indication of non-compliance. In these examples, the updated respective evacuation instructions may include a warning to go back and retrieve a patient 109, medicine 111 and/or a medical device 113 (associated with or unassociated with a particular human asset that has or has not been detected to have been correctly evacuated consistent with initial instructions) that should have been retrieved according to the previous respective evacuation instructions transmitted at the block 306 of the method 300.

However, in other examples, a first one the responders 120 may be having trouble and may need assistance; in these examples, the updated respective evacuation instructions for a second responder 120 may be to assist the first responder 120 and/or to add persons and/or objects to a list of the second responder 120, that were initially on the list of persons and/or objects for the first responder 120 (e.g. that each responder 120 is to evacuate). In yet further examples, an initially determined evacuation route through the building 105 may no longer be viable due to fire, and the like, and the updated respective evacuation instructions may be to reroute a responder 120 through the building 105; however, such rerouting may also occur when a change occurs to persons and/or objects that a responder 120 is retrieve.

Hence, in some examples, the updated respective evacuation instructions for a responder 120 may include, but is not limited to, one or more of: instructions to assist another responder 120; instructions to reroute the responder 120 through the building 105; updated tasks; an updated list of human assets to evacuate from the building 105; an order in which to evacuate the human assets on the updated list of human assets; an updated priority of the human assets; an updated list of physical assets to evacuate from the building 105; an updated order in which to evacuate the physical assets on the updated list of physical assets; and an updated priority of the physical assets.

The updated respective evacuation instructions may also be provided in a visual format and/or aural format and/or HUD format. Indeed, as described above one or more of the communication devices 122 may comprise, and/or be in communication with, a HUD communication device 124, and the respective evacuation instructions and the updated respective evacuation instructions may each be in a HUD format for the HUD communication device 124.

In a particular example, the controller 220 may be further configured to: monitor respective location information of a particular responder 120 to determine when the particular responder 120 has entered a particular portion of the building 105 associated with a particular person or a particular object to evacuate; and determine, via the sensors 107, that the particular person or the particular object is being evacuated from the particular portion of the building 105 along with a plurality of particular secondary objects each associated with the particular person or the particular object, and each associated with a particular one of the sensors 107.

In some of these examples, the particular person may be a patient 109, the particular portion of the building 105 may be a hospital room, the plurality of particular secondary objects may be one or more of required medicines 111 and required medical devices 113, and the sensors 107 are associated with the required medicines 111 or required medical devices 113. In a particular example, a responder 120 may be instructed to evacuate the patient 109-1 with their required medicines 111-4, 111-5, and their required medical devices 113-1, 113-2.

Figure 4:
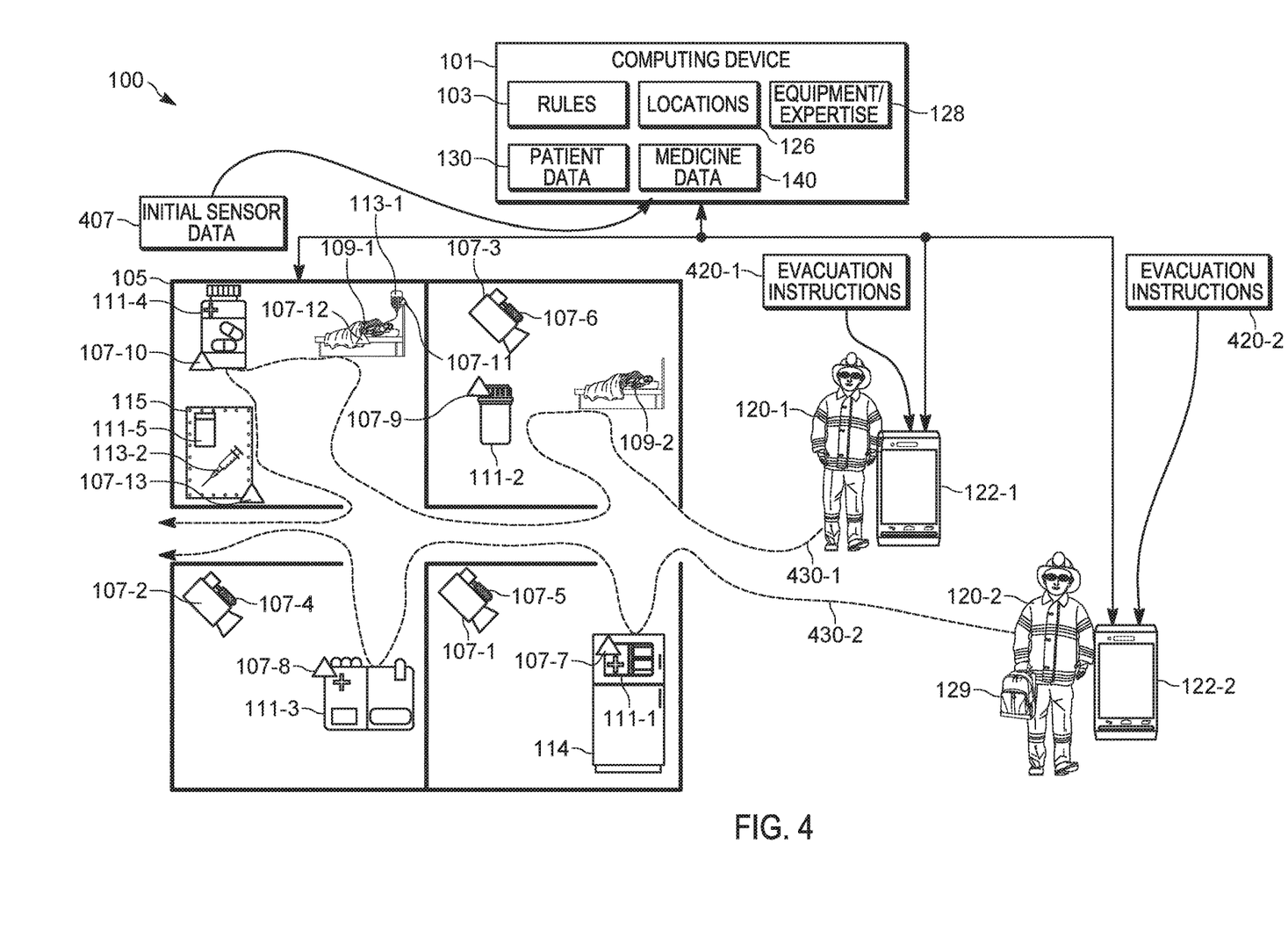
FIG. 4 depicts a portion of a method for evacuation task management being implemented at the system of FIG. 1, in accordance with some examples.
Figure 5:
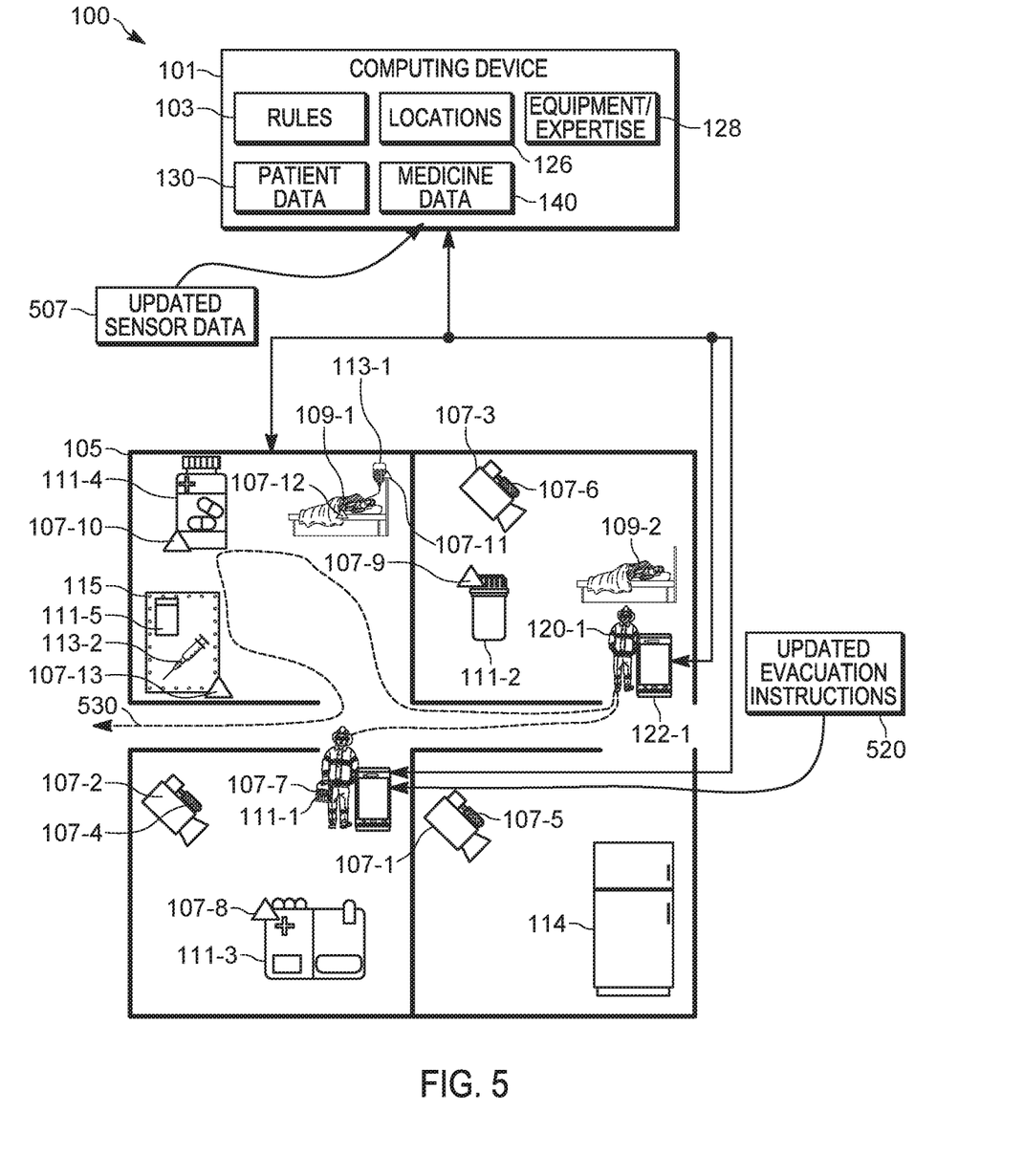
FIG. 5 depicts another portion of the method for evacuation task management being implemented at the system of FIG. 1, in accordance with some examples.

Attention is next directed to FIG. 4 and FIG. 5, each of which are similar to FIG. 1, with like components having like numbers, and which depict an example of the method 300.

With attention directed to FIG. 4, an incident has occurred at the building 105, and the responders 120 have been dispatched thereto. The computing device 101 is receiving (e.g. at the block 302 of the method 300) initial sensor data 407 from the sensors 107. The computing device 101 has furthermore determined a respective location 126 of each of the responders 120, and has received the data 128 indicative of their respective equipment and/or expertise.

The computing device 101 access the electronically stored evacuation rules and generates (e.g. at the block 304 of the method 300) and transmits (e.g. at the block 306 of the method 300) respective evacuation instructions 420-1, 420-2 to the communication devices 122 of the respective responders 120-1, 120-2.

The respective evacuation instructions 420-1, 420-2 may generally include respective routes 430-1, 430-2 that the respective responders 120-1, 120-1 are to follow to implement an evacuation of the building 105. The evacuation instructions 420-1, 420-2 are interchangeably referred to hereafter, collectively, as the evacuation instructions 420, and generically, as a set of evacuation instructions 420. Similarly, the routes 430-1, 430-2 are interchangeably referred to hereafter, collectively, as the routes 430, and generically, as a route 430.

For example, respective evacuation instructions 420-1 are for the responder 120-1 to follow a route 430-1 and may further include instructions for the responder 120-1 to first retrieve the patient 109-2, along with the associated medicine 111-2, and then retrieve the patient 109-1, along with the associated medicines 111-4, 111-5, and the associated medical devices 113-1, 113-2. The responder 120-1 may be dispatched along the route 430-1 to evacuate the patients 109, and associated particular secondary objects (e.g. the medicines 111-2, 111-4, 111-5 and the medical devices 113-1, 113-2) as the responder 120-1 has CPR training. The route 430-1 then takes the responder 120-1 out of the building 105.

Similarly, respective evacuation instructions 420-2 are for the responder 120-2 to follow a route 430-2 and may further include instructions for the responder 120-2 to first retrieve the medicine 111-1 from the refrigerator 114, and for the responder 120-2 to place the medicine 111-1 into the insulated bag 129; the respective evacuation instructions 420-2 may be then to evacuate the medicine 111-3. The responder 120-2 may be dispatched along the route 430-2 to evacuate the medicines 111-1, 111-3 as the responder 120-2 carries the insulated bag 129. The route 430-2 then takes the responder 120-2 out of the building 105.

Each of the respective evacuation instructions 420 may be provided at a respective communication device 122 and/or HUD communication device 124 in visual and/or aural and/or HUD format. For example, the communication device 122 and/or HUD communication device 124 may show a respective route 430 in a respective display screen. Furthermore, when the HUD communication device 124 is providing the respective evacuation instructions 420, such that a responder 120 "sees" assets in a display screen of the HUD communication device 124 (e.g. in an augmented reality environment), assets and/or locations of assets to evacuate may be highlighted in the augmented reality environment. For example, the drawer 115 may be highlighted to show that assets to be retrieved are located therein. Furthermore, when there is more than one asset in an area viewed in the augmented reality environment, the assets may be highlighted in an order of retrieval.

Attention is next directed to FIG. 5 which depicts the system 100 after the responders 120 begin following their respective routes 430. As depicted, however, the responder 120-1 is still attempting to evacuate the patient 109-2 and the associated medicine 111-2. For example, the patient 109-2 may be less mobile than has been recorded in the patient data 130 and/or the patient 109-2 may be suffering from trauma and the responder 120-1 may be administering CPR to the patient 109-2. Regardless, as depicted, the responder 120-1 is delayed and/or may not be complying with the evacuation instructions 420-1.

In contrast, the responder 120-2 is complying with the evacuation instructions 420-2, and has followed the route 430-2 to evacuate the medicine 111-1 into the insulated bag 129 (e.g. along with the attached sensor 107-7). The responder 120-2 has continued along the route 430-2 and is retrieving the medicine 111-3. Hence, the responder 120-2 is generally about to leave the building 105 (e.g. after retrieving the medicine 111-3).

However, as depicted, the computing device 101 continues to monitor sensor data from the sensors 107 and receives (e.g. at the block 308 of the method 300) updated sensor data 507. The computing device 101 further monitors locations 126 of the responders 120. The updated sensor data 507 (e.g. in combination with the locations 126) may indicate that the responder 120-1 is delayed and/or has not yet retrieved any of the assets listed in the evacuation instructions 420-1. Similarly, the updated sensor data 507 may indicate that the responder 120-2 has retrieved (and/or is close to completing retrieving) all the assets listed in the evacuation instructions 420-2. Hence, the updated sensor data 507 may enable the computing device 101 to determine whether the responders 120 are complying with the evacuation instructions 420 and/or whether the responders 120 are delayed and/or need assistance.

As the responder 120-1 is delayed and/or not complying with the evacuation instructions 420-1, and as the responder 120-2 is almost completed the evacuation instructions 420-2, the computing device 101: generates updated evacuation instructions 520 for the responder 120-2 to assist the responder 120-1; and transmits (e.g. at the block 310 of the method 300) the updated evacuation instructions 520 to the communication device 122-2 of the responder 120-2.

As depicted, the updated evacuation instructions 520 include instructions for the responder 120-2 to follow an updated route 530 that takes the responder 120-2 to a current location of the responder 120-1, and then to the patient 109-1, and out of the building 105 (e.g. similar to the route 430-1 followed by the responder 120-1). For example, the updated evacuation instructions 520 include instructions for the responder 120-2 to follow an updated route 530 that takes the responder 120-2 to a current location of the responder 120-1 may be to cause the responder 120-2 to assist the responder 120-1 and/or for information exchange (e.g. to ask whether the responder 120-1 needs assistance and the like). However, in other examples, the updated route 530 may be to bypass the responder 120-1 and route (and/or directly route) the responder 120-2 to the patient 109-1 (e.g. a next patient to which the responder 120-1 was previously assigned to evacuate).

The updated evacuation instructions 520 may then be provided at the communication device 122-2 and/or the HUD communication device 124-2.

Furthermore, the updated evacuation instructions 520 may be provided with a notification that the evacuation instructions for the responder 120-2 have changed, and a reason therefor (e.g. "RESPONDER 120-1 NEEDS ASSISTANCE", for example provided aurally at the communication device 122-2 and/or the HUD communication device 124-2).

The updated evacuation instructions 520 may include additional assets that the responder 120-2 is to evacuate (e.g. the medicine 111-5 and/or the medical device 113-2 associated with the patient 109-1).

Hence, in general, the computing device 101 generates the updated evacuation instructions 520 and/or updated tasks to one or more of change and/or reprioritize and/or reassign tasks amongst the responders 120, assign responders 120 to assist one another, reconfigure what assets to evacuate and/or in what order, determine detours for the responders 120, based on analytics and updated sensor data 507, as well as comparing such received updated sensor data 507 to the rules-based original evacuation instructions 420 and/or tasks. Such functionality may further occur in "real-time". Indeed, the updated evacuation instructions 520 for evacuating the building 105 for each of the responders 120 may comprise an updated prioritization of the human assets and/or the physical assets for evacuation. For example, the updated evacuation instructions 520 may include, but is not limited to an order in which to evacuate the human assets on an updated list of human assets transmitted with the updated evacuation instructions 520 and/or an updated order in which to evacuate physical assets on an updated list of physical assets the updated evacuation instructions 520, each of which may represent an updated priority of the human assets and/or the physical assets as compared to the original evacuation instructions 420.

While not depicted, the computing device 101 may also generate and transmit evacuation instructions to the communication device 122-1 of the responder 120-1, for example to reduce the assets that the responder 120-1 is to evacuate. For example, assets added to the updated evacuation instructions 520 for the responder 120-2 may be removed from updated evacuation instructions for the responder 120-1.

While present examples are depicted for two responders 120, devices, systems and method described herein may be adapted for any suitable number of responders to coordinate evacuation task management of a building. Indeed, the growing ubiquity and connectivity of internet-of-things sensors, and the like, may hence be leveraged to assist in evacuation of buildings to direct responders to perform particular tasks during the evacuation based on generic evacuation rules, as well expertise and equipment of the responders. The sensors may be further used to track compliance with evacuation instructions transmitted to communication devices of the responders, and generate updated evacuation instructions to better ensure compliance and/or to assist other responders.

In the foregoing specification, specific embodiments have been described. However, one of ordinary skill in the art appreciates that various modifications and changes may be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

In this document, language of "at least one of X, Y, and Z" and "one or more of X, Y and Z" may be construed as X only, Y only, Z only, or any combination of two or more items X, Y, and Z (e.g., XYZ, XY, YZ, XZ, and the like). Similar logic may be applied for two or more items in any occurrence of "at least one . . . " and "one or more . . . " language.

Moreover, in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment may be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it may be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

We claim:

1. A computing device comprising:
    a communication unit configured to communicate with:
        sensors distributed throughout a building; and communication devices associated with responders; and
    a controller communicatively coupled to the communication unit and to a memory storing rules for evacuating the building,
    the controller configured to:
        receive, via the communication unit, initial sensor data from the sensors;
        generate respective evacuation instructions for evacuating one or more of persons and objects from the building for each of the responders, the respective evacuation instructions generated from the rules for evacuating the building and the initial sensor data, each person or object associated with at least one of the sensors;
        transmit, via the communication unit, the respective evacuation instructions to a respective communication device of each of the responders;
        monitor, via the communication unit, updated sensor data from the sensors during evacuation of the building and location information associated with each of the responders, to track compliance with the respective evacuation instructions by the responders; and
        transmit, via the communication unit, updated respective evacuation instructions to the respective communication device of one or more of the responders, the updated respective evacuation instructions based on monitored updated sensor data and monitored location information received after transmitting the respective evacuation instructions,
    wherein the controller is further configured to:
        monitor respective location information of a particular responder to determine when the particular responder has entered a particular portion of the building associated with a particular person or a particular object to evacuate; and
        determine, via the sensors, that the particular person or the particular object is being evacuated from the particular portion of the budding along with a plurality of particular secondary objects each associated with the particular person or the particular object and each associated with a particular one of the sensors.

2. The computing device of claim 1, wherein one or more of the initial sensor data and the monitored updated sensor data comprises one or more of:
    images from one or more cameras;
    audio from one or more microphones;
    asset tracking data from one or more asset tracking sensors;
    binary data indicative of one or more of drawers, doors and windows being open or closed, the binary data from one or more drawer sensors, door sensors and window sensors;
    biometric sensor data from one or more biometric sensors; and
    internet-of-things sensor data from internet-of-things sensors.

3. The computing device of claim 1, wherein the rules for evacuating the building comprise one or more of:
    one or more evacuation routes;
    a priority of human assets to be evacuated from the building; and
    a priority of physical assets to be evacuated from the building.

4. The computing device of claim 1, wherein the respective evacuation instructions are further generated from one or more of equipment and expertise of a respective responder accessed at one or more of the memory and the respective communication device of the respective responder.

5. The computing device of claim 1, wherein the respective evacuation instructions for evacuating the building for each of the responders comprise one or more of:
    a route through the building;
    assigned tasks;
    a list of human assets to evacuate from the building along the route;
    an order in which to evacuate the human assets on the list of human assets;
    a list of physical assets to evacuate from the building along the route; and
    an order in which to evacuate the physical assets on the list of physical assets.

6. The computing device of claim 1, wherein the updated respective evacuation instructions for a responder comprises one or more of:
    instructions to assist another responder;
    instructions to reroute the responder through the building;
    updated tasks;
    an updated list of human assets to evacuate from the building;

an order in which to evacuate the human assets on the updated list of human assets;
an updated priority of the human assets; and
a priority of physical assets to be evacuated from the building an updated list of physical assets to evacuate from the building;
an updated order in which to evacuate the physical assets on the updated list of physical assets; and
an updated priority of the physical assets.

7. The computing device of claim 1, wherein the controller is further configured to monitor the updated sensor data during evacuation of the building to track compliance with the respective evacuation instructions by the responders by determining one or more of:
whether a respective responder is following a respective route through the building provided in the respective evacuation instructions;
whether the respective responder is retrieving respective human assets provided in the respective evacuation instructions; and
whether the respective responder is retrieving respective physical assets provided in the respective evacuation instructions.

8. The computing device of claim 1, wherein the controller is further configured to:
when compliance with the respective evacuation instructions is not occurring for a respective responder, include, in the updated respective evacuation instructions for the respective communication device of the respective responder, an indication of non-compliance.

9. The computing device of claim 1, wherein one or more of the communication devices comprises a heads-up display (HUD) communication device, and the respective evacuation instructions and the updated respective evacuation instructions are each in a HUD format for the HUD communication device.

10. The computing device of claim 1,
wherein the particular person is a patient, the particular portion of the building is a hospital room, the plurality of particular secondary objects are one or more of required medicines and required medical devices, and the sensors are associated with the required medicines or required medical devices.

11. A method comprising:
receiving, at a computing device, initial sensor data from sensors distributed throughout a building;
generating, at the computing device, respective evacuation instructions for evacuating one or more of persons and objects from the building for each of responders, the respective evacuation instructions generated from rules for evacuating the building and the initial sensor data, each person or object associated with at least one of the sensors;
transmitting, at the computing device, the respective evacuation instructions to a respective communication device of each of the responders;
monitoring, at the computing device, updated sensor data from the sensors during evacuation of the building and location information associated with each of the responders, to track compliance with the respective evacuation instructions by the responders;
transmitting, at the computing device, updated respective evacuation instructions to the respective communication device of one or more of the responders, the updated respective evacuation instructions based on monitored updated sensor data and monitored location information received after transmitting the respective evacuation instructions,
monitoring respective location information of a particular responded to determine when the particular responder has entered a particular portion of the building associated with a particular person or a particular object to evacuate; and
determining, via the sensory that the particular person or the particular object is being evacuated from the particular portion of the building along with a plurality of particular secondary objects each associated with the particular person or the particular object, and each associated with a particular one of the sensors.

12. The method of claim 11, wherein one or more of the initial sensor data and the monitored updated sensor data comprises one or more of:
images from one or more cameras;
audio from one or more microphones;
asset tracking data from one or more asset tracking sensors;
binary data indicative of one or more of drawers, doors and windows being open or closed, the binary data from one or more drawer sensors, door sensors and window sensors;
biometric sensor data from one or more biometric sensors; and
internet-of-things sensor data from internet-of-things sensors.

13. The method of claim 11, wherein the rules for evacuating the building comprise one or more of:
one or more evacuation routes;
a priority of human assets to be evacuated from the building; and
a priority of physical assets to be evacuated from the building.

14. The method of claim 11, wherein the respective evacuation instructions are further generated from one or more of equipment and expertise of a respective responder accessed at one or more of a memory and the respective communication device of the respective responder.

15. The method of claim 11, wherein the respective evacuation instructions for evacuating the building for each of the responders comprise one or more of:
a route through the building;
assigned tasks;
a list of human assets to evacuate from the building along the route;
an order in which to evacuate the human assets on the list of human assets;
a list of physical assets to evacuate from the building along the route; and
an order in which to evacuate the physical assets on the list of physical assets.

16. The method of claim 11, wherein the updated respective evacuation instructions for a responder comprises one or more of:
instructions to assist another responder;
instructions to reroute the responder through the building;
updated tasks;
an updated list of human assets to evacuate from the building;
an order in which to evacuate the human assets on the updated list of human assets;

an updated priority of the human assets; and a priority of physical assets to be evacuated from the building an updated list of physical assets to evacuate from the building;

an updated order in which to evacuate the physical assets on the updated list of physical assets; and an updated priority of the physical assets.

17. The method of claim 11, further comprising monitoring the updated sensor data during evacuation of the building to track compliance with the respective evacuation instructions by the responders by determining one or more of:

whether a respective responder is following a respective route through the building provided in the respective evacuation instructions;

whether the respective responder is retrieving respective human assets provided in the respective evacuation instructions; and whether the respective responder is retrieving respective physical assets provided in the respective evacuation instructions.

18. The method of claim 11, further comprising:

when compliance with the respective evacuation instructions is not occurring for a respective responder, including, in the updated respective evacuation instructions for the respective communication device of the respective responder, an indication of non-compliance.

19. The method of claim 11, wherein one or more of communication devices associated with the responders comprises a heads-up display (HUD) communication device, and the respective evacuation instructions and the updated respective evacuation instructions are each in a HUD format for the HUD communication device.

20. The method of claim 11, wherein the particular person is a patient, the particular portion of the building is a hospital room, the plurality of particular secondary objects are one or more of required medicines and required medical devices, and the sensors are associated with the required medicines or required medical devices.

* * * * *